United States Patent [19]

Katz et al.

[11] 4,170,827

[45] Oct. 16, 1979

[54] APPARATUS FOR MEASURING HAIR GROWTH

[76] Inventors: Maurice Katz, No. 7 Avenue Marina, Bantry Bay; Kenneth E. Wheeler, 44 Upper Rhine Rd., Sea Point, both of South Africa, 8001

[21] Appl. No.: 858,381

[22] Filed: Dec. 7, 1977

[51] Int. Cl.[2] ............................................. G01B 5/02
[52] U.S. Cl. .............................. 33/125 R; 33/174 D; 128/774
[58] Field of Search ................. 33/125 R, 127, 169 R, 33/174 D; 128/2 S

[56] References Cited

U.S. PATENT DOCUMENTS

| 255,764 | 4/1882 | Brubaker | 33/125 R |
|---|---|---|---|
| 1,962,357 | 6/1934 | Nessler | 33/174 D |
| 1,962,518 | 6/1934 | Nessler | 33/174 D |

FOREIGN PATENT DOCUMENTS 591246  8/1947  United Kingdom .................. 33/125 R Primary Examiner—Richard R. Stearns

[57] ABSTRACT

Apparatus for determining the rate of hair growth by measuring the length of selected hairs at various times. An illuminated transparent member is provided with a recess adapted to receive the hair longitudinally, and to maintain it in an extended condition, and is graduated to visually display the length of the hair. The body area containing the hair to be measured is located by means of a mechanism having two arms, one of which arms is adapted to be placed against a reference point on the body while the other is adjustable to indicate the desired area.

7 Claims, 4 Drawing Figures

APPARATUS FOR MEASURING HAIR GROWTH

BACKGROUND AND SUMMARY OF THE INVENTION

Treatments to retard the growth of facial hair in hirsute females through medication are not practiced in many countries. When such treatment is given, its effectiveness can be accurately assessed only through objective measurement of changes in the rate of hair growth. Many methods used for that measurement lack the necessary accuracy and reproducibility of results. Subjective results from direct examination are largely influenced by expectance levels of both the doctor and the patient, while the examination of photographs taken before and after treatment has been found to lack sensitivity to small fluctuations in the growth rate.

Two methods have been proposed for objective measurement of the rate of hair growth. One involves taking measurements of hair length at selected intervals of time by fitting a graduated capillary tube about a growing hair and gently pressing the end of the tube to the surface of the skin. The image of the hair in the capillary tube is then magnified 16 to 25 times by a Zeiss dermascope for comparison of the hair length with the graduations. However, this method requires the use of sophisticated equipment which is very expensive. Such equipment is also difficult for one operator to handle when used in conjunction with a capillary tube. A second method involves the injection of radioactive sulphur ($S^{35}$). However, this method invades healthy tissue and requires facilities for counting radioactivity. Each of these objective methods is restricted to specialized units due to the nature of the materials and equipment required.

With the aforementioned limitations and deficiencies of known devices in mind, it is an object of the present invention to provide a novel apparatus for accurately measuring the growth rate of hair. More particularly, it is an object to provide an inexpensive and portable apparatus to measure the growth rate of hair which will yield accurate and reproducible results in the hands of technicians of limited training and experience.

Another object of the invention is to provide such an apparatus which may be operated by a single technician.

Yet another object is to provide such a device which includes a graduated tubular member and a light source in which the latter performs the dual function of projecting illumination into the tubular member and also supporting said member.

It is a further object of the invention to provide a simple yet reliable device for the repetitive location of a sample area on a body whose hair growth rate is to be monitored, to enable length measurements to be taken of the hairs in that area at different times.

We have discovered that the above objects and advantages are achieved by a graduated capillary tube or like transparent member having an open end adapted to be placed about a hair to be measured and illuminated with substantially axially directed light for visual comparison of the longitudinal extent of the hair with the graduations. A series of hair length measurements can be made with this instrument at selected intervals of time to determine the growth rate. The capillary tube may have a flattened region in the area of the graduations to enable those graduations to be more easily read. The tube may also be provided with a passage communicating between the atmosphere and the opening into which the hair is received to facilitate the introduction of a liquid such as water into that opening. The presence of the liquid further enhances the readability of the instrument. It is to be understood that when we refer to the tube as being transparent, we mean that the material is sufficiently clear so that a hair can be viewed through it when the tube is illuminated.

The particular area of the body at which the growth rate is to be measured can be repetitively and accurately located with a mechanism which includes two perpendicular arms adjustable relative to each other along their respective axes and having graduations indicating their precise adjustment. One of said arms is adapted to be placed against a suitable reference point on the body while the other has an opening which defines the area of the body where a measurement is to be taken.

DESCRIPTION OF THE PREFERRED EMBODIMENT

Figure 2:
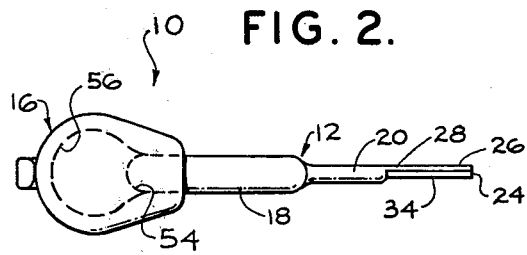
FIG. 2 is a top plan view of the device, taken along the line 2—2 in FIG. 1.
Figure 1:
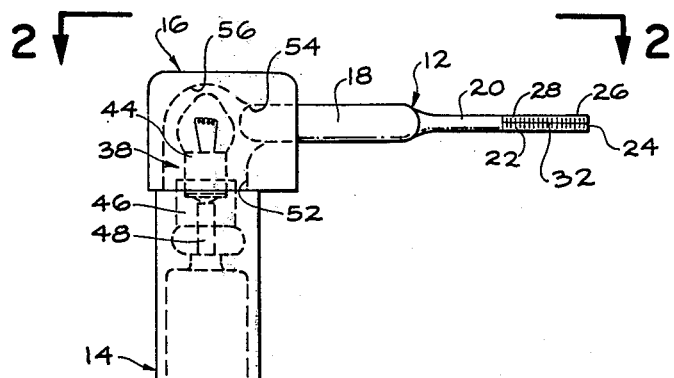
FIG. 1 is a side elevational view of a hair measurement device constructed in accordance with the teachings of the present invention.
Figure 3:
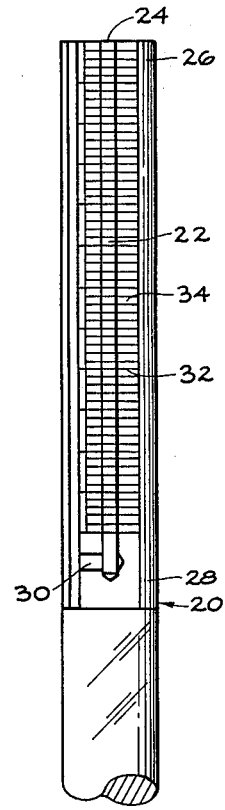
FIG. 3 is an enlarged elevational view of the graduated portion of the device of FIG. 1.

Referring to the drawing more particularly by reference numerals, and particularly FIG. 1, a hair measurement device 10 embodying the teachings of the present invention includes a rod member 12, an illumination apparatus 14, and a transition piece 16.

The rod member 12 includes an upper rod portion 18 to which is affixed a capillary tube 20 in an end-to-end coaxial relationship. An axially directed cylindrical recess 22 extends from an opening 24 in the remote end 26 of the capillary tube 20 to a closed end 28 displaced axially therefrom. The diameter of the recess 22 is somewhat larger than the diameter of a hair, the length of which is to be measured. The recess 22 may communicate with the atmosphere adjacent the closed end 28 through an air vent 30 which extends in a direction perpendicular to the axis of the tube 20. The air vent 30 therefore facilitates the introduction of a liquid such as water into the recess. Graduations 32, located on a longitudinal flat region 34 of the exterior of tube 20, denote the length of the tube 20 from its end 26.

The capillary tube 20 may be constructed of cylindrical glass or clear acrylic stock having an outside diameter of 2.2 mm. The recess 22 may have a diameter of 0.34 mm. while the graduations 32 may be provided at 0.2 mm distances for a length of 12 mm.

The upper rod portion 18 is constructed of either a transparent or translucent material to allow light transmittance from the transition piece 16 to the capillary tube 20.

The illumination apparatus 14 comprises a tubular housing 36, a lamp and socket arrangement 38, batteries 40 and an end cap 42. The lamp and socket arrangement 38 includes a lamp 44 which fits within a socket 46 to contact a conductive element 48. It is fixed within one end of the tubular housing 36 such that the lamp 44 projects outwardly in an axial direction from the housing 36. The batteries 40 are located within the housing 36 in series such that one of their end terminals contacts the conductive member 48. The end cap 42 is removably connected to the housing 36 and is provided with a spring 50 which contacts the lower end terminal of the batteries 40 and biases those batteries in an upward direction against the conductive element 48. The housing 36 and the end cap 42 are either constructed of conductive materials or provided with conductive paths to complete the circuit between the spring 50 and the lamp 44. Power is thus supplied to the lamp 44 by the batteries 40.

The transition piece 16 is provided with circular openings 52 and 54 communicating through a cavity 56. The illumination apparatus 14 is connected to the transition piece 16 at the opening 52 such that the lamp 44 projects into the cavity 56 and a light-tight seal is formed between the opening 52 and the housing 36. The upper rod portion 18 is fitted within the opening 54 and directed toward the lamp 44 within the cavity 56. Light from the lamp 44 is therefore allowed to escape from the transition member 16 only by way of the rod member 12. This results in light transmittance essentially axially along the capillary tube 20, illuminating said tube to facilitate comparison of the extent of the hair being measured with the graduations 32.

It will be noted that the illumination apparatus 14 and the transition piece 16 performs the dual function of providing illumination through the rod member 12 and also supporting said rod member in a rigid manner.

In operation, the capillary tube 20 is fitted about a hair (not shown) whose length is to be measured, such that the hair extends axially through the opening 24 and along the recess 22. When remote end 26 contacts the skin at the base of the hair, the graduation 32 which coincides with the end of that hair represents the length. The flat region 34 of the tube 20 and the axial light from the lamp 44 aid in comparing the graduations 32 with the hair. Comparison can be further aided by filling the recess 22 with a liquid such as water. The air vent 30 enables this to be done.

A simple magnifying glass or loupe may also be used to magnify the graduated area, if desired.

Figure 4:
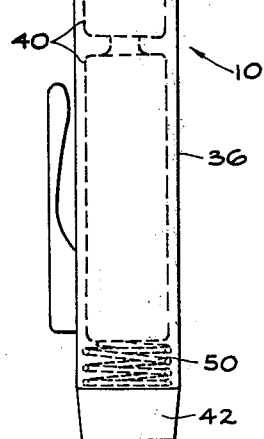
FIG. 4 is a front elevational view of a location device constructed in accordance with the teachings of the invention for use in conjunction with the measurement device shown in FIGS. 1-3.
Figure 4:
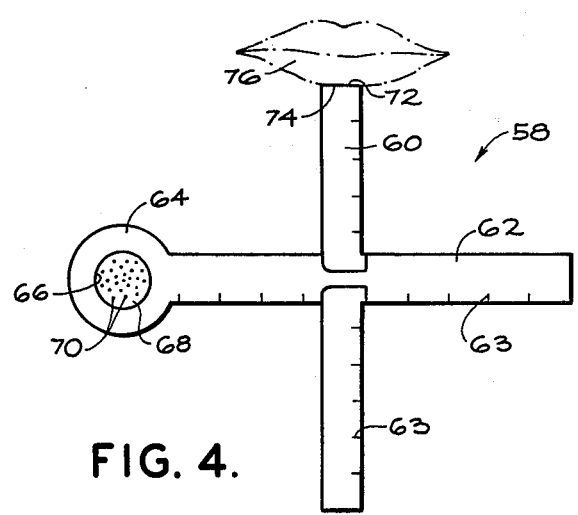

Referring to FIG. 4, a location device 58 may comprise two perpendicular arms 60 and 62 which are connected together and contain graduated markings 63. The arm 62 is slidably adjustable along its axis relative to the arm 60 and is provided at one end with an annular portion 64 having a circular opening 66. Said opening defines a limited body area 68 containing hairs 70 to be measured.

The arm 60 may also be constructed to be slidably adjustable along its axis relative to the arm 62.

In operation, the arm 60 is placed in a specified position relative to a reference point on a body whose hair is to be measured. In the case illustrated in FIG. 4, the arm 60 is positioned vertically with its upper end 72 directly beneath the vermillion border 74 of the mid lower lip 76 of a human subject. Alternatively, one of the graduations 63 of the arm 60 may be aligned with the vermillion border 74 to yield a different reference position. The arm 62 can be adjusted with the aid of the graduations 63 to a particular axial position, exposing the narrowly defined area 68 containing the desired group of hairs 70 within the circular opening 66. Once the reference position and the graduation corresponding to the axial position of the arm 62 are recorded, the same group of hairs can be consistently located with the device 58 for further measurement.

The rate of hair growth can therefore be simply and accurately determined by taking successive length measurements of one or more of the hairs 70 within the area 68. The increase in hair length between measurements, when divided by the time lapsed, yields the growth rate.

The length of the various hairs in an area may be standardized by shaving the area before the initial measurement is taken. This minimizes errors which might otherwise occur when an operator is unable to relocate the precise hairs initially measured. It is thus not critical that the same hairs in the group be measured each time.

While one specific embodiment of the invention has been disclosed as typical, the invention is of course not limited to the particular form shown and described, but rather is applicable broadly to all variations as fall within the scope of the appended claims.

We claim:

1. A device for measuring hair length, which comprises in combination:
   a transparent tubular member having an axial passageway and an open end adapted to receive a hair whose length is to be measured and to maintain the hair in an extended condition;
   graduations on said member corresponding to the length of said member from the open end; and
   means supporting said tubular member and for projecting light into it to facilitate visual comparison of the longitudinal extent of the hair with said graduations.

2. A device as recited in claim 1, in which said transparent member comprises a capillary tube having an open end with an axial bore diameter slightly greater than the diameter of the hair.

3. A device as recited in claim 2, in which the exterior surface of the capillary tube in the area of said graduations is of planer configuration.

4. A device as recited in claim 3, in which said means for projecting light into said transparent member comprises a light source and a means for directing light from the source essentially axially along said member.

5. A device as recited in claim 4, in which the capillary tube is open at a second position spaced from the open end to facilitate the reception of a liquid within the open end by allowing a path for air to escape from the interior of the tube.

6. A device as recited in claim 5, in which said means for directing light includes an essentially opaque housing attached to the light source for minimizing the escape of light therefrom other than in the direction of the tube.

7. A device as recited in claim 6, in which said light source comprises a miniature battery-operated incandescent lamp.

* * * * *